(12) United States Patent
Barbour

(10) Patent No.: US 7,471,975 B2
(45) Date of Patent: Dec. 30, 2008

(54) OPTICAL TENSOR IMAGING

(75) Inventor: Randall L. Barbour, Glen Head, NY (US)

(73) Assignee: The Research Foundation of State University of New York, Albany, NY (US)

( * ) Notice: Subject to any disclaimer, the term of this patent is extended or adjusted under 35 U.S.C. 154(b) by 248 days.

(21) Appl. No.: 11/232,847

(22) Filed: Sep. 22, 2005

(65) Prior Publication Data

US 2006/0064001 A1    Mar. 23, 2006

Related U.S. Application Data

(60) Provisional application No. 60/611,998, filed on Sep. 22, 2004.

(51) Int. Cl.
*A61B 6/00* (2006.01)
(52) U.S. Cl. .............. 600/473; 600/476; 600/407; 600/310
(58) Field of Classification Search ............. 600/473, 600/476, 407, 310; 356/432
See application file for complete search history.

(56) References Cited

FOREIGN PATENT DOCUMENTS

WO    WO 01/20305    *    3/2001

OTHER PUBLICATIONS

Taylor, Charles A. et al. "In Vivo Quantification of Blood Flow and Wall Shear Stress in the Human Abdominal Aorta During Lower Limb Exercise", Annals of Biomedical Engineering, vol. 30, p. 402-408, 2002.*
Day, Steven W. et al. "Particle Image Velocimetry Measurements of Blood Velocity in a Continuous Flow Ventricular Assist Device", ASAIO Journal, vol. 47(4), pp. 406-411, Jul.-Aug. 2001.*

* cited by examiner

*Primary Examiner*—Eric F Winakur
*Assistant Examiner*—Katherine L Fernandez
(74) *Attorney, Agent, or Firm*—Scully, Scott, Murphy & Presser, P.C.

(57) ABSTRACT

A method of measuring local and propagating pulsatile behavior of a vasculature system provides a way to non-invasively measure vascular dynamics and, in particular, allows for objective measurement of the propagating expansion-contraction waves. The method includes capturing a time-series of optical images, and analyzing the images to produce a time-series of vector field maps based on measurements of local displacement of hemoglobin contrast. The method further includes obtaining a resulting time-dependent tensor field image and analyzing the resulting time-dependent tensor field image to obtain metrics of local and propagating oscillatory behavior.

14 Claims, 5 Drawing Sheets

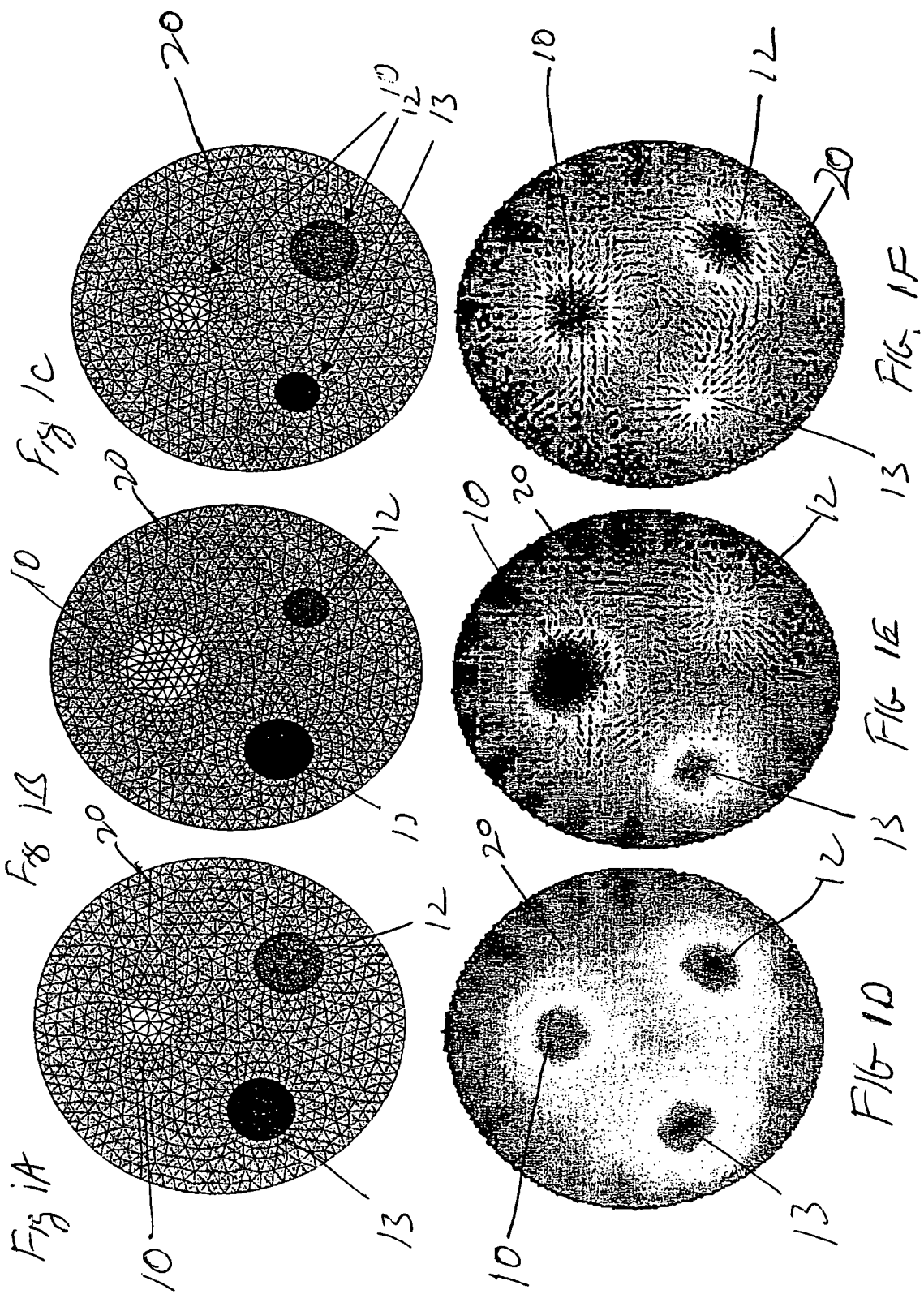

OPTICAL TENSOR IMAGING

CROSS REFERENCE TO RELATED CASES

This application claims priority to and the benefit of Provisional U.S. Patent Application Ser. No. 60/611,998, filed Sep. 22, 2004, the entirety of which is incorporated herein by reference.

FIELD OF THE INVENTION

The invention relates generally to imaging of tissues and, more particularly, to imaging of vascular dynamics of deep tissue structures including actions that influence blood redistribution in tissue.

BACKGROUND OF THE INVENTION

Adequate delivery of blood to tissue is an essential element to maintaining health and normal tissue function. At the level of the microvasculature, this process is tightly regulated through coordinated interactions involving the autonomic nervous system, local metabolic effectors, and hormonal agents. One effect of these actions is to produce rhythmic oscillations in tissue perfusion thereby limiting the demand on the heart that would otherwise be required should continuous perfusion of tissue be required throughout the body. Modulation of this behavior is considered an important component in regulating blood pressure and in the redistribution of blood from the periphery to critical central organs during shock, among other actions. Damage to this blood redistribution mechanism is thought to be a component of a variety of disease processes, in particular, those involving autonomic dysfunction. One example is the condition known as orthostatic intolerance, wherein the normal increase in blood pressure accompanying a rise from the recumbent to standing position does not occur and results in syncope.

The details of oscillatory behaviors associated with the microvascular bed in living tissue have been studied under a variety of experimental conditions and are believed to arise from two principal mechanisms. Under neural control are the Traube-Hering-Mayer waves. These are thought to entrain large areas of tissue and serve to modulate regional changes in blood delivery to tissue. Local oscillations arise from vasomotion, which is thought to be mainly responsive to autoregulatory mechanisms. On a macroscopic level, these behaviors produce two types of phenomenology including local oscillatory behavior and propagating oscillatory behavior with the latter arising from coordinated expansion-contraction cycles. While these behaviors are widely recognized, their detailed study in intact living tissues has been mainly limited to surface examinations using the laser Doppler technique. Characterization of these behaviors in deep tissue structures could have considerable practical value but until recently has not been possible. One approach that is suitable for deep tissue studies is the method of acoustic Doppler imaging. This technique, while suitable for examining large vessels, is insensitive to the microvascular bed, which is the component of the vascular tree believed to be mainly responsible for the considered dynamics. A sensing technology is needed that is sensitive to the dynamics of the microvascular bed in deep tissues. Further, an analysis approach is needed that can define the considered phenomenology.

SUMMARY OF THE INVENTION

The invention relates generally to imaging of tissues and, more particularly, to imaging of vascular dynamics of deep tissue structures including actions that influence blood redistribution in tissue.

In one aspect, the invention relates to a method of measuring local and propagating pulsatile behavior of a vasculature system. The method includes capturing a time-series of optical images, and analyzing the images to produce a time-series of vector field maps based on measurements of local displacement of hemoglobin contrast. The method further includes obtaining a resulting time-dependent tensor field image, and analyzing the resulting time-dependent tensor field image to obtain metrics of local and propagating oscillatory behavior.

In one embodiment, the optical images include near infrared optical tomographic images. In another embodiment, capturing a time-series of optical images includes using DC frequency domain or ultrafast illumination-detection methods. In still another embodiment, capturing a time-series of optical images comprises using photoacoustic, acoustic modulation of light fields, or diffuse correlation tomography. In other embodiments, the vector field images are associated with blood redistribution, and the vector field images are computed using image velociometry. In another embodiment, the oscillatory behavior comprises expansion and contraction waves.

In another aspect, the invention relates to a method of dynamic vascular imaging. The method includes performing non-invasive imaging to obtain a time-series of images of a hemoglobin signature within the vasculature, characterizing a propagating or pulsing behavior of the hemoglobin signature within the vasculature based on the time-series of images; and providing at least one image that identifies a direction and magnitude of the propagating or pulsing behavior.

In one embodiment, the hemoglobin signature includes oxyhemoglobin, deoxyhemoglobin, total hemoglobin, or hemoglobin oxygen saturation. In another embodiment, performing non-invasive imaging includes performing dynamic optical tomography. In still another embodiment, characterizing a propagating or pulsing behavior includes using particle imaging velocimetry. In yet another embodiment, providing at least one image that identifies a direction and magnitude of the propagating or pulsing behavior includes using velocity vectors throughout an image map.

The foregoing and other objects, aspects, features, and advantages of the invention will become more apparent from the following description and from the claims.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

FIGS. 1A-1C are illustrative finite element models each including three inclusions undergoing pulsating contractions according to one embodiment of the invention.

FIGS. 1D-1F depict reconstructed images including overlaid velocity vectors according to another embodiment of the invention.

DETAILED DESCRIPTION OF THE INVENTION

Figure 2A:
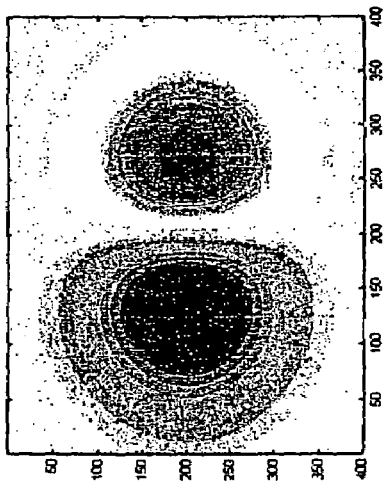
FIGS. 2A-2L illustrate a PIV analysis of an image time-series according to one embodiment of the invention.
Figure 2B:
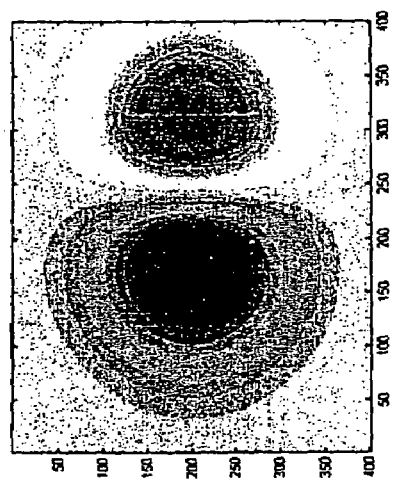
Figure 2C:
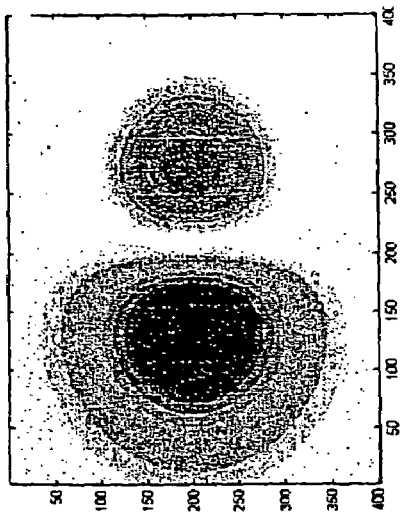
Figure 2D:
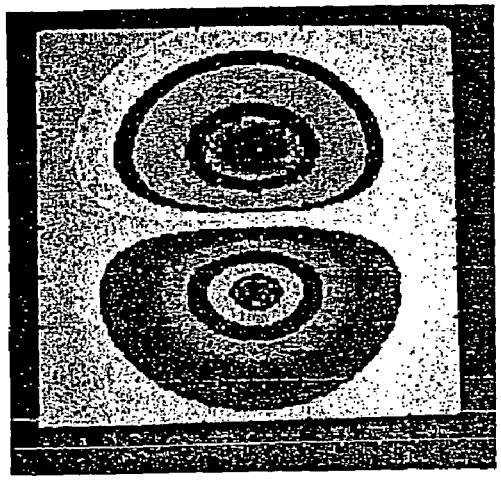
Figure 2E:
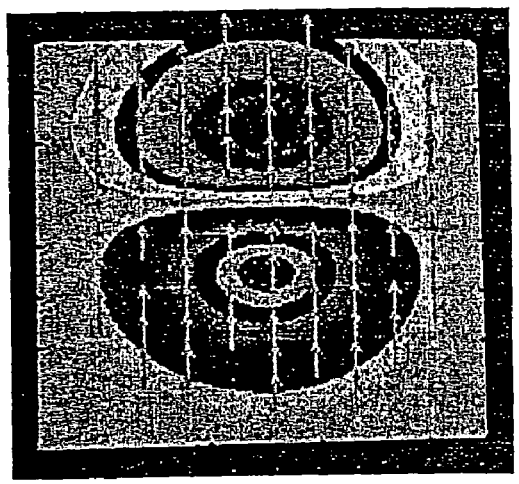
Figure 2F:
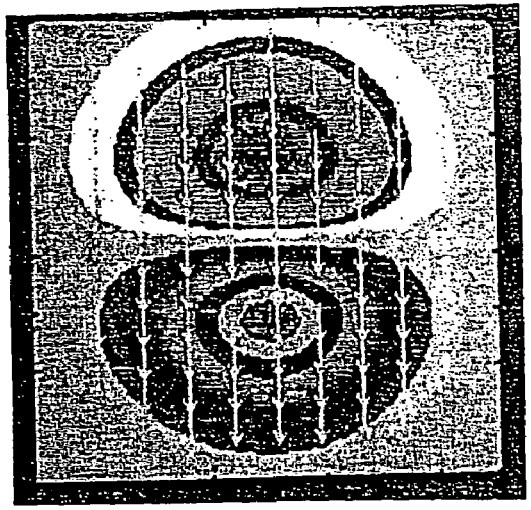
Figure 2G:
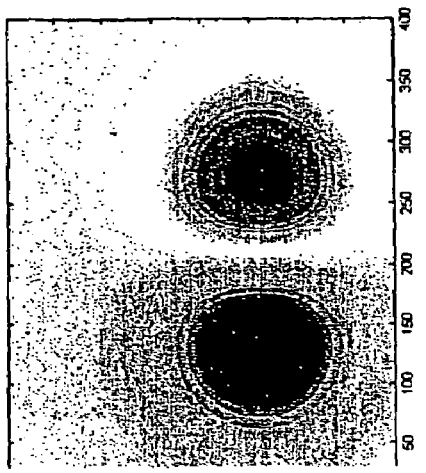
Figure 2H:
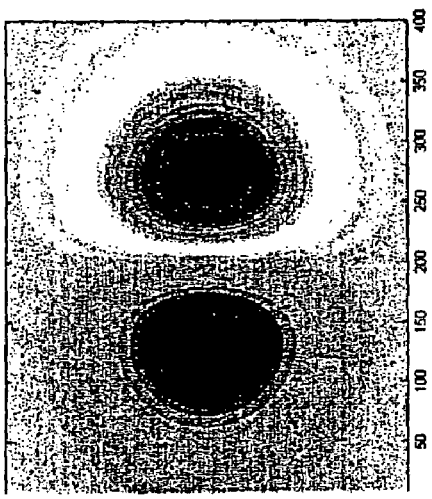
Figure 2I:
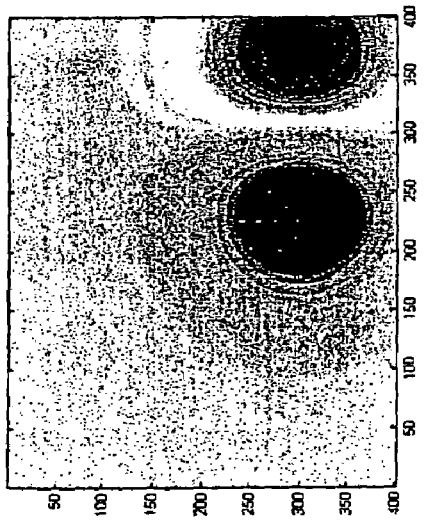
Figure 2J:
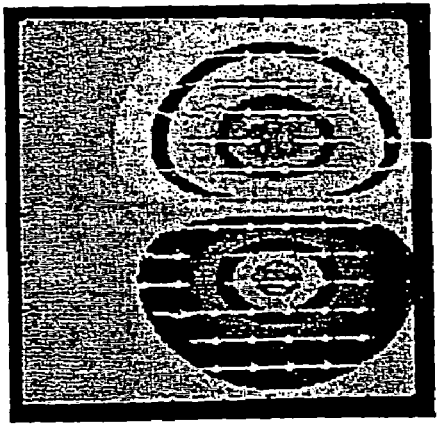
Figure 2K:
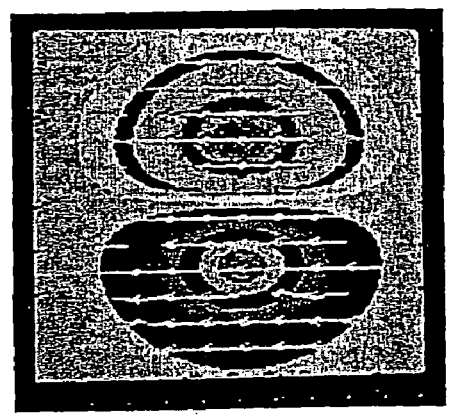
Figure 2L:
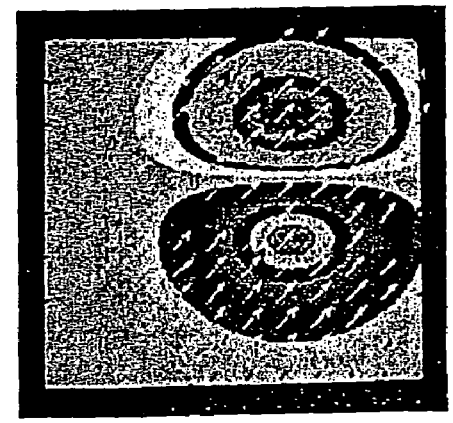

The present invention provides a method for characterizing the local and propagating aspect of pulsatile behaviors of the vasculature. In particular, the method provides a way to non-invasively measure these forms of vascular dynamics and, in particular, allows for objective measurement of the propagating expansion-contraction waves.

The present invention also provides a method for dynamic vascular imaging that includes performing non-invasive imaging, such as dynamic optical tomography, to obtain a time-series of images of the vasculature of a subject human or other mammal, characterizing a propagating and/or pulsing behavior of the vasculature based on the time-series, such as by using Particle Imaging Velocimetry (PIV), and providing at least one image that identifies a direction and magnitude of the propagating and/or pulsing behavior, such as by using velocity vectors throughout an image map. These measurements can be used to monitor a wide range of functional states having clinical and investigative significance including measurements for diagnostic or prognostic purposes, monitoring responses to therapy or guiding therapy, or defining actions of pharmaceuticals.

The method involves acquiring a time-series of near infrared optical tomographic images and subjecting these to analysis that defines vector fields associated with blood redistribution as seen by differences in the time-dependent hemoglobin contrast maps. Computation of these vector fields can be accomplished using any of a variety of methods.

In one embodiment, the vector fields are computed using image velociometry, which is a technique widely used by the fluid dynamics community. Measurements are derived from either a 2D or 3D image time-series and applied to any of the available hemoglobin signals including oxyhemoglobin, deoxyhemoglobin, total hemoglobin, or hemoglobin oxygen saturation.

In another embodiment, measurements are obtained using injectable absorbing or fluorescing dyes, which themselves could be modified using appropriate molecular targeting vehicles. In other embodiments, the optical imaging information needed to generate the vector field maps could be obtained using any of a variety of illumination-detection techniques and image formation schemes. These techniques include, but are not limited to, use of DC, frequency domain, or ultrafast illumination-detection methods employed for generating images based on diffuse optical signals. In still other embodiments, the measurements could also be derived from other optical-based imaging techniques including use of photoacoustic, acoustic modulation of light fields, or diffuse correlation tomography.

The described method builds upon the known technique of diffuse optical tomography and, in particular, its use in obtaining a time-series of images from tissue measurements. Briefly, this involves performing an optical array measurement that provides for the capture of emerging light field intensities as a function of one or more source positions. In other embodiments, approaches are used that employ one or more illuminating wavelengths of light in the near infrared region so as to provide for improved tissue penetration and to allow for the characterization of hemoglobin states using spectroscopic analysis methods. It is expressly understood that any of a number of illumination-detection techniques can be employed and include continuous wave (DC), frequency domain using RF modulated light sources, or ultrafast techniques that provide for the detection of light intensities on a picosecond to nanosecond scale, for example.

Image recovery from the resulting tomographic data sets can be accomplished using any of a number of reconstruction techniques. In one embodiment, the invention contemplates the Normalized Difference Method described by Pei et al. (U.S. patent application publication no. 2004/0010397, published Jan. 15, 2004, entitled "Modification Of The Normalized Difference Method For Real-Time Optical Tomography", and incorporated herein by reference) in either the Born or Rytov approximation. In still other embodiments, these approaches can be extended beyond the first order solution to include nonlinear updates (e.g., Newton Raphson techniques). However, for the purposes of the example given, first order solutions are considered.

Because the quality of the recovered image will influence the fidelity of the recovered dynamics (e.g., propagating and non-propagating oscillations), image enhancement techniques such as described by Barbour et al's Frequency Encoding of Spatial Information (FESI) (PCT publication no. WO 03/012736, published Jan. 15, 2004, entitled "Method And System For Enhancing Solutions To A System Of Linear Equations", and incorporated herein by reference) and Temporal Encoding of Spatial Information (TESI), i.e., linear deconvolution methods (See U.S. patent application Ser. No. 10/894,317, filed Jul. 19, 2004, entitled "Image Enhancement By Spatial Linear Deconvolution", and incorporated herein by reference) are also contemplated by the present invention.

The significance of these approaches is that they can correct for the linear spatial convolution component that is invariably introduced when employing algebraic reconstruction methods and thereby provide for significantly improved images with a minimum of computational overhead. Accordingly, as an example, a direct current (DC) illumination approach that provides for the capture of a tomographic time-series of images involving one or more illuminating wavelengths and for which the resulting data set is evaluated using the NDM method with or without additional processing involving the TESI or FESI approach in either the first order Born or Rytov approximation is considered. Further, in other embodiments, the above-described method is used to generate either 2D or 3D images.

In one embodiment, to identify and characterize nonpropagating dynamic behavior, the resulting time-series of images is subsequently subjected to any of a variety of standard signal processing techniques. In some embodiments, it is preferable to employ blind source separation techniques (e.g., principal component analysis, independent component analysis) to allow for the quantitative separation of overlapping time varying behaviors. In other embodiment, time-frequency and time correlation methods are used to allow for improved characterization of local dynamics and for identifying spatio-temporal correlations in the image maps.

In some embodiments, methods commonly employed in the field of fluid dynamics such as Particle Imaging Velocimetry (PIV) and the Minimum Quadratic Difference (MQD) are used to identify and characterize propagating dynamic behavior. The PIV technique allows for the identification of velocity vectors throughout an image field, thereby generating a tensor array that serves to identify the direction and magnitude of propagating dynamics associated with the vascular bed (e.g., Mayer waves). This technique is typically applied to evaluate particle movement. However, in one embodiment of the present invention, this technique is use to track bulk displacement of the hemoglobin signal, arising from actions of Mayer waves and vasomotion, from one timepoint to the next. The PIV method computes particle movement by determining the magnitude and direction of the temporal derivative caused by local particle movement, or as envisioned here, by local bulk displacement of the hemoglobin signal. For each time-interval considered, a vector field map can be derived thereby producing a time-varying tensor field. Analysis of the time-varying tensor field serves to define a range of local phenomenologies, including those arising from coordinated spatial displacement of the hemoglobin signal reflecting propagating actions of the microvascular bed. This analysis can be achieved in many ways. For example, in one embodiment, for any given region-of-interest, the time-varying spatial propagation of the local vectors is determined by concatenating one vector at time point one to the corresponding displaced vector at time point two an so on. This will produce a trajectory describing the spatial-temporal propagation associated with vascular dynamics arising from vasomotion and Mayer waves. The details of these trajectories are expected vary depending on the health status of tissue and the actions of drugs.

In other embodiments, other forms of analysis are applied including methods commonly used in signal processing (e.g., time correlation, time-frequency, temporal decomposition, etc.), and those used to explore nonlinear dynamic phenomenology (e.g., correlation dimension of attractor, maximum Lyapunov exponent, etc.)

The fidelity of the identified vector fields can be expected to vary with the quality of the reconstruction methods, and thus it is important to use techniques that are robust to expected uncertainties of experimental measurements (e.g., imperfect knowledge of boundary conditions, variable optical coupling with the tissue surface, inaccuracy in measuring system calibration, etc.).

Yet, another important consideration is the use of techniques that are computationally efficient such as the NDM method with or without additional image enhancement using the TESI or FESI methods.

Referring to FIGS. 1A-1F, shown is an example of computed vector fields (FIGS. 1D, 1E, and 1F) following the steps outlined above from a simulated dense scattering medium representing tissue 20 containing blood vessels 10, 12, 13 whose diameters are varying in time. The images shown were computed using the NDM method for a DC source-detector array placed along the boundary of the medium. Note that comparison of the vector fields (FIGS. 1D, 1E, 1F) to the original target (FIGS. 1A, 1B, 1C, respectively) reveals that the computed tensor image correctly captures the oscillating behavior.

Referring to FIGS. 2A-2L, in one embodiment, a PIV analysis of an image time-series is shown. In this example, propagating behaviors are represented by movement of an object along various paths within the dense scattering medium. FIGS. 2A-2C and 2G-2I, represent the simulated medium, and FIGS. 2D-2F and 2J-2L, respectively, represent the corresponding vector fields. Here, the propagating dynamics are correctly identified regardless of the path taken within the medium. An example of the simulated behavior shown in FIGS. 2A-2L is the vascular reactivity associated with Mayer waves involving the microvascular bed.

Figure 3B:
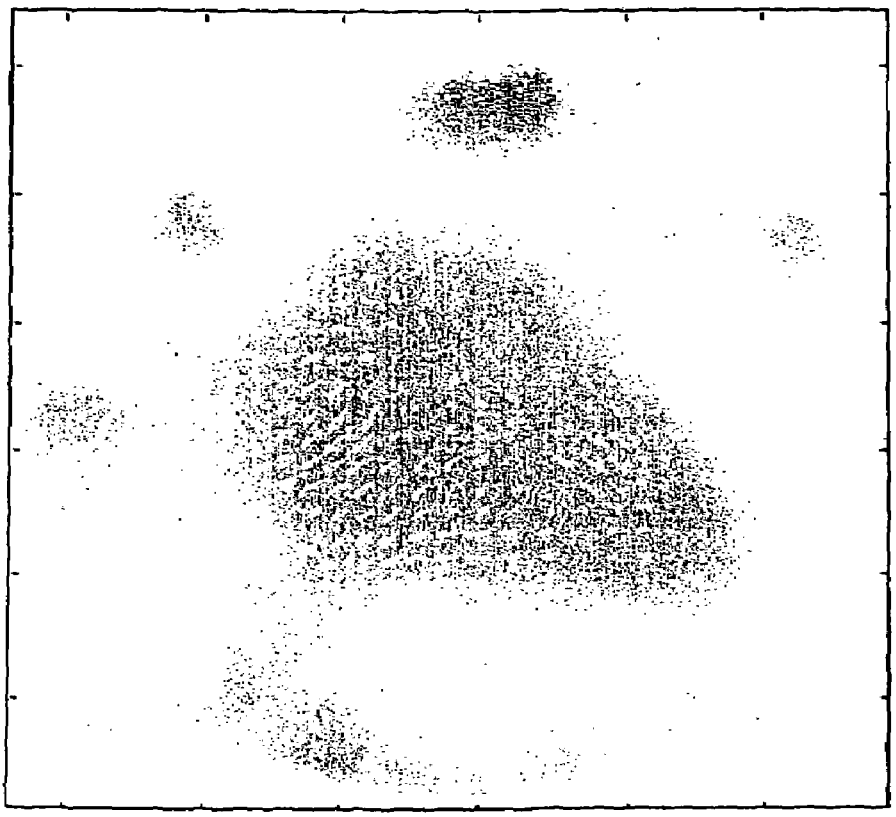
FIGS. 3A and 3B illustrate an overlay of computed vector fields at two different time points on a corresponding 2D cross sectional absorption image of the human forearm, according to another embodiment of the invention.
Figure 3A:
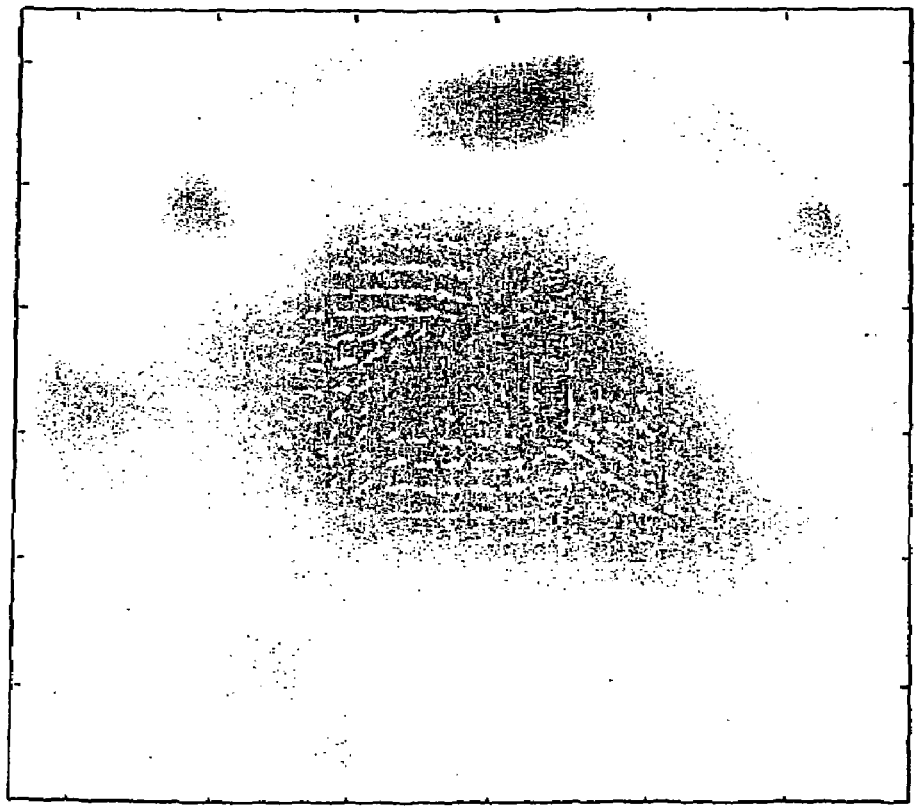
Figure 4B:
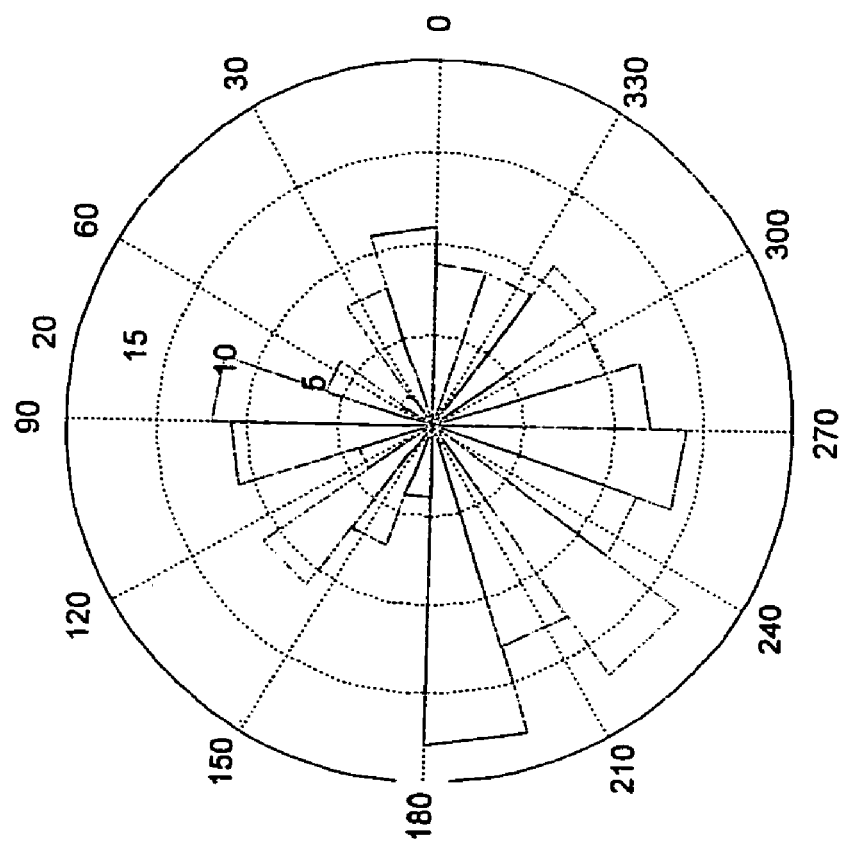
FIG. 4B depicts a polar plot of a directional dependence of a vector field in localized regions in an image map for a long term diabetic, according to another embodiment of the invention.
Figure 4A:
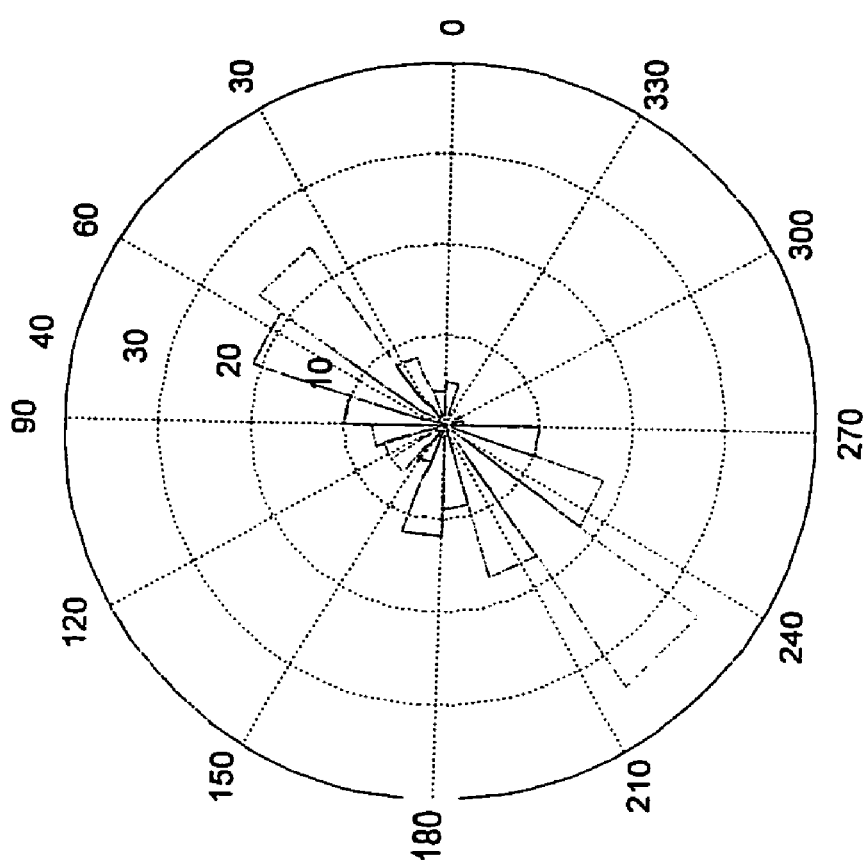
FIG. 4A depicts a polar plots of a directional dependence of a vector field in localized regions in an image map for a healthy individual, according to one embodiment of the invention.

Referring to FIGS. 3A and 3B, in one embodiment, an overlay of computed vector fields at two different time points on a corresponding 2D cross sectional absorption image of the human forearm is shown. This overlay was obtained from an analysis of a time-series of 2D images collected from the forearm of a healthy volunteer. Inspection shows clear evidence of coordinated behavior throughout the image of the types depicted in FIGS. 1A-1F and FIGS. 2A-2L. In addition, careful inspection of the time-dependence of the vector field in localized regions of the image map shows that this behavior is decidedly limited in direction over modest time intervals (30-60 sec) and contrasts the nearly isotropic response seen from corresponding data collected from an individual with long-term diabetes, which is shown in FIGS. 4A and 4B.

Thus, in accordance with the methods outlined above, we can observe spatially coordinated propagating behaviors whose dyscoordination is linked to functional disturbances of the vascular bed. Moreover, in other embodiments, multiple sites in the body are observed concurrently to gain further insights.

The methods outlined above can serve as a general approach to detection, characterization, and discrimination of various disease states, as a monitoring strategy for acute care medical procedures, monitoring responses to drug therapy, and for examining the actions of pharmaceutical agents in laboratory animals and human subjects. Particular applications include, but are not limited to, breast cancer detection and monitoring, assessment of peripheral vascular disease, and a broad spectrum of applications in neuropsychiatry and related fields. The latter include, for example, the detection of deceit (i.e., lie detector), learning disorders, senile dementia, and the occurrence of stroke and its rehabilitation. Other clinical applications include, but are not limited to, measures under emergency field conditions, intensive care units, or with ambulatory subjects. Animal studies can include small animals used in laboratory studies or for veterinary uses involving small and large animals.

Further still, the above-described method can be used in combination with other physiological measures such as absorbing/fluorescing dyes, and other directed therapies, for example.

Variations, modifications, and other implementations of what is described herein may occur to those of ordinary skill in the art without departing from the spirit and scope of the invention. Accordingly, the invention is not to be defined only by the preceding illustrative description.

What is claimed is:

1. A method of measuring local and propagating pulsatile behavior of a vasculature system, comprising:
    capturing a time-series of optical images;
    analyzing the images to produce a time-series of vector field maps based on measurements of local displacement of hemoglobin contrast;
    obtaining a resulting time-dependent tensor field image for each time-interval being considered, from said time-series of vector field maps; and
    analyzing the resulting time-dependent tensor field image to obtain metrics of local and propagating oscillatory behavior.

2. The method of claim 1 wherein the optical images comprise near infrared optical tomographic images.

3. The method of claim 1 wherein capturing a time-series of optical images comprises using DC frequency domain or ultrafast illumination-detection methods.

4. The method of claim 1 wherein capturing a time-series of optical images comprises using photoacoustic, acoustic modulation of light fields, or diffuse correlation tomography.

5. The method of claim 1 wherein the vector field images are associated with blood redistribution.

6. The method of claim 1 wherein the vector field images are computed using image velociometry.

7. The method of claim 1 wherein the oscillatory behavior comprises expansion and contraction waves.

8. A method of dynamic vascular imaging, comprising
performing non-invasive imaging to obtain a time-series of images of a hemoglobin signature within the vasculature;
characterizing a propagating or pulsing behavior of the hemoglobin signature within the vasculature based on the time-series of images; and
providing at least one image that identifies a direction and magnitude of the propagating or pulsing behavior of said vasculature; and
determining time-varying spatial propagation of local vectors associated with a region-of-interest from said identified direction and magnitude by concatenating one vector at time point one to corresponding displaced vector at time point two.

9. The method of claim 8 wherein the hemoglobin signature comprises oxyhemoglobin, deoxyhemoglobin, total hemoglobin, or hemoglobin oxygen saturation.

10. The method of claim 8 wherein performing non-invasive imaging comprises performing dynamic optical tomography.

11. The method of claim 8 wherein characterizing a propagating or pulsing behavior comprises using particle imaging velocimetry.

12. The method of claim 8 wherein providing at least one image that identifies a direction and magnitude of the propagating or pulsing behavior comprises using velocity vectors throughout an image map.

13. The method of claim 1, wherein said analyzing step further includes at least:
determining time-varying spatial propagation of local vectors associated with a region-of-interest from said vector field maps by concatenating one vector at time point one to corresponding displaced vector at lime point two.

14. The method of claim 1, wherein said analyzing step further includes at least:
defining a trajectory describing spatial-temporal propagation associated with vascular dynamics arising from vasomotion.

* * * * *